United States Patent [19]

Schreiner

[11] Patent Number: 4,937,887
[45] Date of Patent: Jul. 3, 1990

[54] GARMENT WITH HOOK-AND-LOOP FASTENERS

[75] Inventor: David N. Schreiner, Montreal, Canada

[73] Assignee: Med-I-Pant Inc., Montreal, Canada

[21] Appl. No.: 253,617

[22] Filed: Oct. 5, 1988

[30] Foreign Application Priority Data

Jul. 29, 1988 [CA] Canada .................................. 573463

[51] Int. Cl.$^5$ ........................ A41B 9/00; A41B 17/00
[52] U.S. Cl. ............................................ 2/402; 2/406; 2/237; 604/385.1; 604/385.2
[58] Field of Search .................. 2/DIG. 6, 237, 221, 2/197, 128, 141 R, 141 A, DIG. 11, 402, 406; 24/306, 442; 604/385.1, 385.2

[56] References Cited

U.S. PATENT DOCUMENTS

| | | | |
|---|---|---|---|
| 2,198,738 | 4/1940 | Pintus | 2/237 |
| 2,447,850 | 8/1948 | Feldman | 2/197 |
| 2,756,432 | 7/1956 | Beregow et al. | 2/128 |
| 2,999,246 | 9/1961 | Rowan | 2/221 |
| 3,164,844 | 1/1965 | Ruby | 2/221 |
| 4,011,600 | 3/1977 | Malk | 2/197 |
| 4,023,212 | 5/1977 | Huffman | 2/DIG. 6 |
| 4,089,068 | 5/1978 | Swallow | 2/221 |

FOREIGN PATENT DOCUMENTS

| | | | |
|---|---|---|---|
| 1460048 | 1/1969 | Fed. Rep. of Germany | 2/221 |
| 797688 | 7/1958 | United Kingdom | 2/237 |
| 912994 | 12/1962 | United Kingdom | 2/237 |
| 1100047 | 1/1968 | United Kingdom | 2/237 |

Primary Examiner—Werner H. Schroeder
Assistant Examiner—Jeanette E. Chapman
Attorney, Agent, or Firm—McFadden, Fincham, Marcus & Allen

[57] ABSTRACT

In a garment, such as briefs or diapers for incontinent patients, which employ hook-and-loop fasteners, impairment of fastener operation by accumulation of lint on the hook-fastener tab is avoided by storing the hook-fastener tab in a pocket of the garment when the garment is being laundered. Preferably, the hook-fastener tab is secured in the pocket by elastic material so that it can be extended, stretching the elastic material, to fasten it to the corresponding female or loop-type fastener tab and will automatically be retracted into the pocket by the elastic material, as soon as it is released. The pocket may comprise PVC or other semi-rigid pliable smooth material and may be fabricated together with the fastener tab separately from the garment and attached to it is a "retrofit". Alternatively, it may be formed integrally with the garment.

10 Claims, 1 Drawing Sheet

GARMENT WITH HOOK-AND-LOOP FASTENERS

This invention relates to garments of the kind having so-called hook-and-loop type fasteners, and is especially applicable to garments in the form of briefs or diapers for incontinent patients, infants, and liners or covers for such garments.

The invention is particularly concerned with problems arising from the use of the hook-and loop type fasteners with such garments. Such fasteners, for example, are marketed under the trade mark VELCRO (registered trade mark) usually comprise two pads, one on each of the two pieces of the garment to be fastened together. One pad, conveniently referred to as the "male", has a multiplicity of resilient hooks protruding from its surface. The other pad, conveniently referred to as the "female" has a pile formed by a plurality of loops or loop-like projections. When the male pad is pressed flat onto the female pad, the hooks engage in the loops. A drawback for such hook-and-loop fasteners is that the male fastener pad can collect lint during laundering of the garment which reduces the efficiency of the fastener. This problem is significant when the garments need to be laundered frequently, as is the case with diapers and other incontinency garments. A further problem can arise during laundering in that the male fastener pad can snag other garments, perhaps causing damage.

In order to solve this problem, it has been proposed to seal or completely cover the male fastener pad, during laundering, using an extra female fastener pad. Canadian Patent No. 1,212,204 to Frederica V. Coates discloses such a garment fastener arrangement in which two different embodiments are employed. On the one hand, the closure pad is provided on a flap which is hinged at one end to the male pad to be obscured, and closes onto it through a small angle. In the other embodiment, the extra female pad is provided on the same strip of material as the male pad to be obscured, which is folded back on itself to seal and prevent lint accumulation.

It is desirable for the sealing flap or pad to close automatically onto the male fastener pad because it is likely to be forgotten when the garment is being prepared for laundering. It has been proposed, in the case of the hinged type of closure flap, to rely upon the stitching along the hinge axis, to bias the flap onto the male fastener pad. This is not entirely satisfactory, however, since such hook-and-loop type fasteners usually require positive pressure to close one against the other and the mere biasing by means of stitching will not provide such positive closure.

An object of the present invention is to provide a garment with hook-and-loop type fasteners which eliminates the deficiencies recounted in the foregoing discussion.

According to the present invention, a garment having hook-and-loop type fastening means, has a loop-type fastener pad secured or associated with a first part of the garment, a pocket associated with a second part of the garment, a hook-fastener tab housed in said pocket and extendable therefrom to overlie and engage said loop-type fastener pad, and means for retracting said hook-fastener tab into said pocket.

The retracting means comprises a retracting device preferably in the form of elastic ligament connecting the male fastener tab to the interior of the pocket. The lengths of the hook-fastener tab, ligament, and pocket are preferably arranged so that an end portion of the hook-fastener tab will protrude from the pocket when the hook-fastener tab is in the retracted position and thus serve as a pull-tab.

In preferred embodiments of the invention, the pocket is constructed integrally with the garment. It is envisaged, however, that the pocket could be fabricated separately, complete with elastic and fastener tabs, and attached to the garment after its manufacture.

Advantageously, the pocket comprises a sleeve of synthetic plastics material so that it will not snag the hooks of the hook-fastener tab. Moreover, at least the mouth of the pocket may be bound with a material that is relatively smooth so that the male fastener tab does not snag as it enters the pocket.

One form of the invention is where the garment comprises a diaper such as an adult diaper as will be illustrated hereinafter; the particular materials from which the components of the present invention can be made can vary and will be obvious to those skilled in the art after reading the present disclosure. Thus, the embodiment where a diaper is employed may utilize conventional diaper forming materials; the pocket which may be a synthetic plastic material as noted above, may likewise be made of other material for different applications such as fabric materials. Likewise, a hook and fastener may be made of materials such as those referred to above e.g. "Velcro".

Various advantages will be seen from the illustrated embodiments and as otherwise described herein.

An embodiment of the invention will now be described by way of example only, and with reference to the accompanying drawings, wherein.

Figures 2A, 2B:
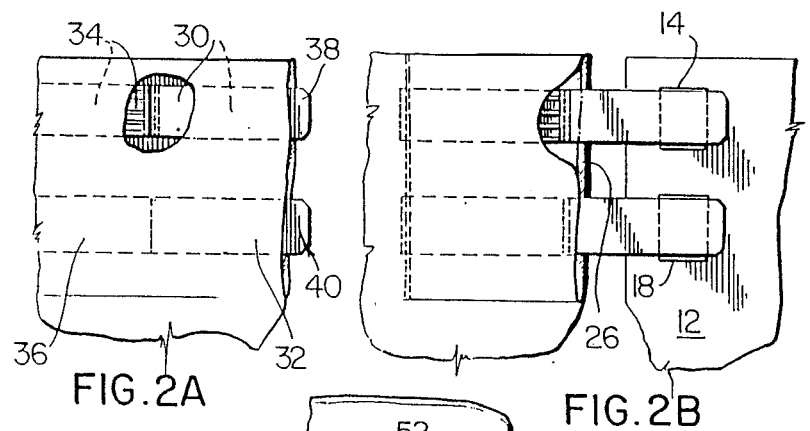
FIG. 2a shows a quick release fastener portion of the diaper with the fastening tabs retracted.

FIG. 2b corresponds to FIG. 2a with the fastener tabs extended; and

Figure 1:
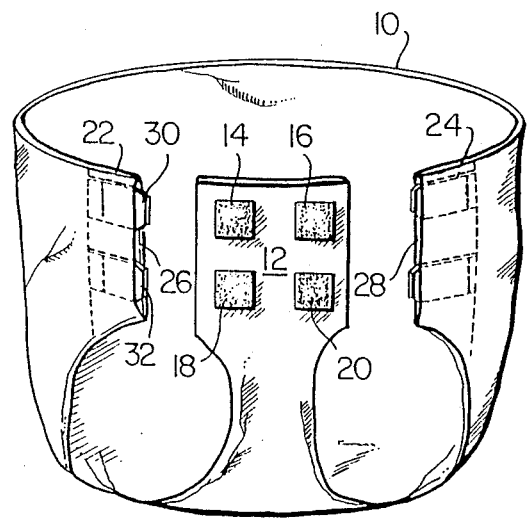
FIG. 1 shows a diaper or brief for use in incontinency.
Figure 3:
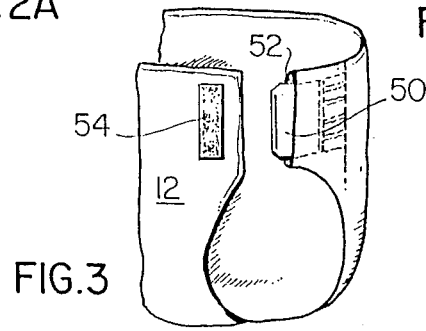

FIG. 3 is a partial view of a diaper modified to have a single fastener tab instead of two as shown in FIG. 1.

Referring now to FIG. 1, an adult brief 10, of generally hourglass shape when flat, is shown in the form it would assume, when worn, just prior to closing of its fasteners. The construction of brief 10 is as disclosed in Canadian Patent No. 1,205,251, and briefly, comprises an exterior moisture-impermeable barrier layer and an inner soft liner layer. Between the outer barrier and the inner soft layer are provided one or more layers of highly absorbent material to absorb moisture passing into the garment through the liner layer. When the brief is being fitted, a frontal flap 12 is passed between the legs from front to rear and extends upwards onto the abdomen. The frontal flap 12 carries loop-type fastener pads 14, 16, 18 and 20, respectively. Tabs 14 and 18 are disposed one above the other adjacent one lateral edge and tabs 16 and 20 similarly disposed adjacent the other lateral edge of the flap. Flank or wing portions 22 and 24, respectively, of the brief 10 extend one around each side of the torso to meet the lateral edges of the frontal flap 12. In the flank portions 22 and 24, at the edge portion that is juxtaposed to the frontal flap 12, are provided pockets 26 and 28, respectively. (See FIGS. 2a and 2b). The pocket comprises a sleeve of vinyl or polyvinyl chloride (FIG. 2a) which is fitted between the outer and inner layers of the brief. Although PVC is preferred, other semi-rigid pliable, smooth materials could be used, the intention being to minimize the risk of snagging by a pair of hook-fastener tabs 30 and 32, respectively, housed inside the pocket.

The hook-fastener tabs 30 and 32 are connected by elastic ligaments 34 and 36, respectively, to the interior of the pocket 26. The elastic ligaments 34 and 36 are conveniently stitched at one end to the respective fastener tab and at the other end of the pocket. If the tabs and pocket sleeve are installed as the garment is being made, the stitching of the interior end of the pocket, which secures the interior ends of the elastic ligaments 34 and 36, can be done at the same time that the pocket is secured in the garment. As shown in FIG. 1 and 2a, the fastener tabs 30 and 32 are positioned, when in the retracted position, so that their end portions 38 and 40, respectively, protrude beyond the mouth of the pocket 26. Hence the end portions 38 and 40 can be grasped to withdraw the fastener tabs 30 and 32 from the pocket and secure them onto the corresponding female or loop-type fastener pads 14 and 18, respectively. It should be noted that the male or hook-fasteners are provided on the reverse surface of the fastener tabs 30 and 32 in FIG. 2a. When the fastener tabs 30 and 32 are released from the female pads 14 and 18 they will automatically be withdrawn or retracted into the pocket 26 by means of the elastic ligaments 34 and 36, respectively. Hence, there will be no danger of them accumulating lint during laundering of the brief 10.

The pocket 28 has a corresponding pair of fastener tabs to cooperate in a similar manner with the female fastener pads 16 and 20 respectively.

The mouths of the pockets 26 and 28 have linings which are of a smooth material to facilitate retraction and extraction of the hook-fastener tab without snagging on the edge of the pocket.

FIG. 3 shows a modification in which a single fastener tab 50 housed in a pocket 52 cooperates with a single female fastener pad 54 on the frontal flap 12. Otherwise, the construction is similar to that illustrated in FIG. 1.

It will be appreciated that automatic retraction of the hook fastener tab to a storage position inside the pocket 26 is advantageous in preventing accumulation of lint on the hooks. A further advantage, however, derives from the use of elastic to return the fastening tab, since elastication enhances the comfort and fit of the brief as compared with garments in which the fastenings, once made, are fixed or static, allowing the garment to conform to body shape and movement more readily than a fastener that does not incorporate elasticity. Moreover, the avoidance of extra flaps or tabs which are redundant when the brief or diaper is being worn, leads to a neater appearance and the elasticated tabs are easy to use, inconspicuous and durable.

As mentioned previously, the pocket may be provided integrally during manufacture of the garment, with the benefit that it appears and feels an integral part of the whole garment. On the other hand, however, the pocket with fastening tabs within it could be made as a separate unit, with an outer fabric cover, and attached to the brief. This would allow easy repair or replacement or retrofitting of existing garments.

I claim:

1. A diaper having a main portion for extending around the rear of the lower torso of a person, and having opposed side edges; a frontal flap for extending between the legs of the person and up between said opposed side edges, said flap having side edges for positioning adjacent the side edges of said main portion to form pairs of adjacent side edges; hook-and-loop fastening means on each of said pairs of adjacent side edges, said fastening means comprising a loop-type fastener pad on one side edge of each pair of adjacent side edges, a pocket on the other side edge of each pair, a hook-type fastener tab housed therein and extendable therefrom so as to overlie and engage said loop-type fastener pad on the adjacent side edge when said main portion and said frontal portion are juxtaposed, elastic means for maintaining said hook-type fastener tab into said pocket to prevent lint accumulation thereon during laundering and wherein said hook-type fastener tab is extendable from said pocket to engage said loop type fastener pad upon pulling said hook-type fastener tab from said pocket, said pocket having non-snaggable material on the interior surfaces opposed to said hook-type fastener tab to prevent catching of said hook-type fastener tab in said pocket.

2. A garment as defined in claim 1, wherein said elastic means comprises an elastic ligament connecting said hook fastener tab to the interior of said pocket.

3. A garment as defined in claim 1, wherein said hook fastener tab has an end portion which can be grasped to withdraw said hook fastener tab from said pocket when said hook-fastener tab is in a retracted condition.

4. A garment as defined in claim 1, wherein said pocket is integral with the garment.

5. A garment as defined in claim 1, wherein said pocket and hook-fastener tab comprise a unit fabricated separately from said garment.

6. A garment as defined in claim 1, wherein the mouth of the pocket has a binding of relatively smooth fabric.

7. A garment as defined in claim 1, wherein said pocket includes a sleeve of synthetic plastics material.

8. A fastening arrangement as defined in claim 1, wherein said pocket houses a pair of said hook-fastener tabs to extend substantially parallel to one another.

9. A garment as claimed in claim 1, wherein said loop-type fastener pad is on said frontal flap and said pocket is on said main portion.

10. A garment as claimed in claim 9, wherein said side edges of said main portion are in adjacent non-overlapping juxtaposition to said side edges of said frontal portion, when said hook fastener tab overlies and engages said loop fastener pad.

* * * * *